United States Patent

Stack et al.

Patent Number: 4,539,407
Date of Patent: Sep. 3, 1985

[54] β-CARBOLINE ANTICONVULSANTS

[75] Inventors: Gary P. Stack, Merion; John A. Moyer, West Chester, both of Pa.

[73] Assignee: American Home Products Corporation, New York, N.Y.

[21] Appl. No.: 696,820

[22] Filed: Jan. 31, 1985

Related U.S. Application Data

[63] Continuation of Ser. No. 561,006, Dec. 13, 1983.

[51] Int. Cl.³ .......................................... C07D 209/56
[52] U.S. Cl. ...................................... 546/87; 546/86; 546/85
[58] Field of Search ...................... 546/86, 87

[56] References Cited

U.S. PATENT DOCUMENTS 3,646,045  2/1972  Berger et al. ...................... 546/86

Primary Examiner—Henry R. Jiles
Assistant Examiner—Johann Richter
Attorney, Agent, or Firm—George Tarnowski

[57] ABSTRACT

There are disclosed compounds of the formula

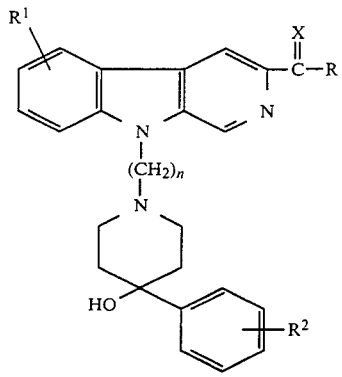

wherein
X is O, S or $NHR^3$, wherein $R^3$ is hydrogen, lower alkyl or cycloalkyl;
R is loweralkyl, loweralkoxy, aralkoxy of up to 10 carbon atoms or $NR^4R^5$ wherein $R^4$ and $R^5$ are, independently, hydrogen, lower alkyl, cycloalkyl or aminoalkyl; or R is alkoxymethyl or hydroxymethyl;
n is one of the integers 2, 3 or 4;
$R^1$ and $R^2$ are, independently, hydrogen, halo, nitro, cyano, $SCH_3$, or $NR^6R^7$, $NHCOR^6$, $COOR^6$, $OR^6$ or $SO_2NR^6R^7$ wherein $R^6$ and $R^7$ are independently hydrogen or loweralkyl;
and their activity as anticonvulsants, having use in the treatment of epileptic conditions.

2 Claims, No Drawings

β-CARBOLINE ANTICONVULSANTS

This is a continuation of application Ser. No. 561,006 filed Dec. 13, 1983.

DESCRIPTION OF THE INVENTION

This invention relates to novel β-carboline-3-carboxylate ester derivatives having anticonvulsant activity.

Since Braestrup et al. [*Proceeding of the National Academy of Sciences*, U.S.A., 77(4), 2288-92 (1980)] found that ethyl-β-carboline-3-carboxylate, a compound obtained during organic solvent extraction of human urine, possesses a high affinity for binding to the benzodiazepine receptors, efforts have been carried out to elucidate the pharmacological activity of this and similar compounds. It has been established that ethyl-β-carboline-3-carboxylate is a potent proconvulsant, capable of reversing the anti-convulsant actions of the benzodiazepines. The methyl and propyl esters of β-carboline-3-carboxylic acid display a more varied neuropharmacological profile. Thus, while they are also potent inhibitors of $^3$H-flunitrazepam receptor binding, the methyl ester is a proconvulsant while the propyl ester is not, and further, the methyl ester is a potent convulsant, producing convulsions that are blocked by the ethyl and propyl esters [See Oakley and Jones, *Neuropharmacology*, 21, 587-9 (1982)].

A series of 3-substituted-β-carboline derivatives is disclosed in European patent application No. 54,507 which are also capable of strongly displacing $^3$H-flunitrazepam from the benzodiazepine receptors found in the central nervous system of vertebrates. Moreover, these compounds are disclosed to be potent inhibitors of aggression and demonstrate a moderate anti-convulsive activity. Because of these effects and because the compounds are anxiolytic, they are disclosed to be useful in the treatment of anxiety and tension, unrest, pathological aggressiveness and the like.

The compounds of the invention, which have the formula

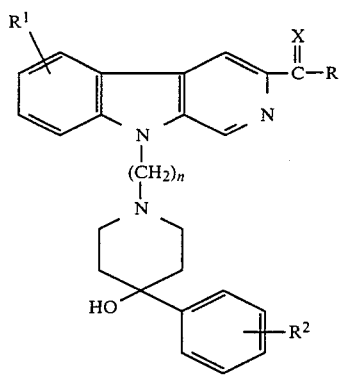

wherein
X is O, S or NHR$^3$, wherein R$^3$ is hydrogen, loweralkyl or cycloalkyl;
R is loweralkyl, loweralkoxy, aralkoxy of up to 10 carbon atoms or NR$^4$R$^5$ wherein R$^4$ and R$^5$ are, independently, hydrogen, loweralkyl, cycloalkyl or aminoalkyl; or R is alkoxymethyl or hydroxymethyl;
n is one of the integers 2, 3 or 4;
R$^1$ and R$^2$ are hydrogen, halo, nitro, cyano, SCH$_3$, or NR$^6$R$^7$, NHCOR$^6$, COOR$^6$, OR$^6$ or SO$_2$NR$^6$R$^7$ wherein R$^6$ and R$^7$ are independently hydrogen or lower alkyl;
are potent anti-convulsants, which are devoid of any other significant neuropharmacological activity, being non-anxiolytic with minimal sedative activity and low potential for anti-psychotic activity.

The term "lower alkyl" and "lower alkoxy" refer to moieties having 1 to 6 carbon atoms in the carbon chain. The term "cycloalkyl" refers to moieties having rings of 3 to 7 carbon atoms. The term "halo" refers to fluoro, chloro, bromo and iodo.

The compounds of the invention can be prepared according to the following reaction sequence:

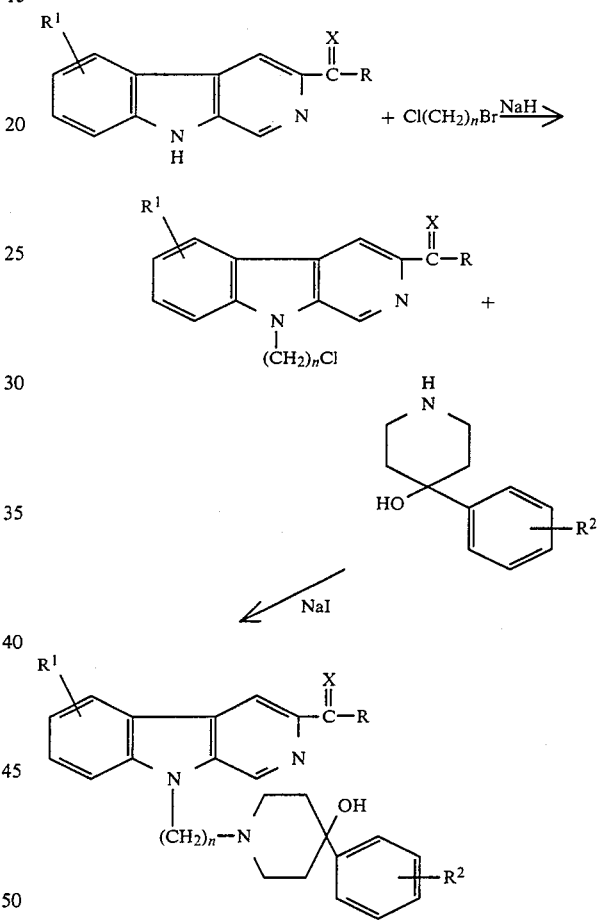

wherein X, R, R$^1$, R$^2$ and n are as hereinbefore defined. The first reaction is carried out in dimethylformamide at room temperature under a nitrogen atmosphere. The second reaction is carried out in organic solvent at elevated temperatures. The starting compounds, i.e., the 3-substituted-β-carboline derivatives are available commercially or can be prepared by conventional methods. For example, loweralkyl esters of β-carboline-3-carboxylic acid can be prepared according to the procedure of King and Stiller, *J. Chem. Soc.*, 1937, 466 ff.

The compounds of the invention, by virtue of their substantially pure anticonvulsant activity, are useful in the treatment of epilepsy. Moreover, because the compounds exhibit little sedative activity, their use in the treatment of epilepsy is not attended by the central nervous system adverse reactions which occur with many of the drugs currently available for the treatment of epileptic conditions.

When the compounds of the invention are employed in the treatment of epileptic conditions, they can be formulated into oral dosage forms, such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic.

The dosage requirements vary with the particular compositions employed, the route of administration, the severity of the symptoms presented and the particular subject being treated. Treatment will generally be initiated with small dosages less than the optimum dose of the compound. Thereafter, the dosage is increased until the optimum effect under the circumstances is reached. In general, the compounds of the invention are most desirably administered at a concentration that will generally afford effective results without causing any harmful or deleterious effects, and can be administered either as a single unit dose, or if desired, the dosage may be divided into convenient subunits administered at suitable times throughout the day.

The pharmacological profile of the compounds of the invention is demonstrated by standard pharmacological procedures, which are described more fully in the examples given hereinafter. These procedures illustrate the ability of the compounds of the invention to antagonize pentylenetetrazol-induced tonic convulsions, and to antagonize seizures in the mouse minimal/maximal electroshock test. The compounds are also tested in procedures to examine their activity as anxiolytics, sedatives, and antipsychotics, as well as to establish their ability to inhibit benzodiazepine receptor binding.

The following examples show the preparation and pharmacological testing of the compounds of the invention.

EXAMPLE 1

9-[3-[4-(4-Chlorophenyl)-4-hydroxyl-1-piperidinyl]-propyl]-9H-pyrido[3,4-b]indole-3-carboxylic acid ethyl ester

A.

9-(3-chloropropyl)-9H-pyrido[3,4-b]indole-3-carboxylic acid ethyl ester

To 10 g. (41.6 mmoles) of ethyl-β-carboline-3-carboxylate in 500 ml of dimethylformamide is added 2.0 g (50 mmoles) of 60% NaH-mineral oil dispersion. This mixture is stirred at room temperature under $N_2$ for 30 minutes, then 18.8 g (0.12 moles) of 1-bromo-3-chloropropane is added. The mixture is stirred at room temperature under $N_2$ for 24 hours. The solvent is then removed in vacuo and replaced with 500 ml of methylene chloride. The mixture is washed with 250 ml each of 2N HCl, saturated aqueous sodium bicarbonate, saturated brine and dried over $Na_2SO_4$. Filtration, evaporation, and column chromatography on 200 g of silica gel with chloroform as eluent gives 7.5 g of yellow solid (58%). A sample recrystallized from isopropanol gives a white solid, m.p. 128°–129° C., with the following analytical data:

Analysis for: $C_{17}H_{17}N_2O_2Cl$: Calculated: C, 64.44; H, 5.41; N, 8.84. Found: C, 64.27; H, 5.39; N, 8.60.

IR (KBr): 1683 cm$^{-1}$.

NMR (CDCl$_3$): 1H singlet 9.05δ, 1H singlet 8.9δ, 1H doublet 8.3δ, 3H mult 7.5δ, 4H mult 4.6δ, 2H trip 3.55δ, 2H quint 2.4δ S, 3H triplet 1.5δ.

B.

9-[3-[4-(4-Chlorophenyl)-4-hydroxy-1-piperidinyl]-propyl]-9H-pyrido[3,4-b]-indole-3-carboxylic acid ethyl ester 7.5 g of 9-(3-chloropropyl)-3-carbethoxy-β-carboline is dissolved in 500 ml of acetone and 17 g (0.11 mole) of sodium iodide is added. The mixture is stirred for 2 days at room temperature, filtered, and evaporated. 500 ml of methylene chloride is added, the mixture washed with dilute aqueous sodium thiosulfate, water, saturated brine and dried over sodium sulfate. It is filtered and evaporated. 250 ml of DMF is added, along with 4.2 g (20 mmole) of 4-(p-chlorophenyl)-4-hydroxypiperidine and 2.4 g (24 mmole) of triethylamine and the mixture is heated at 50°–60° C. in an oil bath for 12 hours. The solvent is removed in vacuo and replaced with 500 ml $CH_2Cl_2$. It is washed with 250 ml each of saturated aqueous sodium bicarbonate, saturated brine and dried over sodium sulfate. Filtration, evaporation, column chromatography (200 g of silica with 7% ethanol, 0.5% NH$_4$OH in methylene chloride) and recrystallization from HCl/isopropanol, then from ethanol gives 3 g of white solid (m.p. 210°).

Analysis for: $C_{28}H_{30}N_3O_3Cl.HCl.H_2O$: Calculated: C, 61.50; H, 5.90; N, 7.69. Found: C, 60.55; H, 5.94; N, 7.79.

IR (KBr): 3400, 2950, 1710 cm$^{-1}$.

NMR (d$_6$ DMSO, free base): 1H(s) 9.0δ, 1H(s) 8.9δ, 1H(d) 8.3δ, 7H(m) 7.5δ, 4H(m) 4.6δ, 13H envelope 1.7–2.8δ, 3H(t) 1.5δ.

EXAMPLE 2

The anticonvulsant activity of a compound of the invention is determined by its ability to antagonize pentylenetetrazol-induced clonic and tonic convulsions. The procedure is carried out as follows:

Test compounds, suspended or solubilized in 0.25% Tween 80 ® in water are administered at several dose levels to 20–25 gm male CF-1 mice (6/dose level). One hour later, all animals are challenged with pentylenetetrazol (Metrazol ®, 155 mg/kg). The incidence of clonic and tonic convulsions and deaths is then observed for one-half hour. Clonic convulsions are discriminated from tonic convulsions on the basis of extensive rigidity and extensor position noted in the tonic condition. Protection against convulsions and death is determined by comparison to control animals run simultaneously with experimental animals.

The incidence of clonic and tonic convulsions and death is recorded for each experimental/control group.

Antipentylenetetrazol ED$_{50}$ values and 95% confidence intervals for antagonism of clonic and tonic convulsions and protection against death are calculated by the Spearman-Karber method.

The ED$_{50}$ and 95% confidence intervals (mg/kg) for standard compounds in this procedure are as follows:

| Drug | Route | Clonic Convulsion | Tonic Convulsion | Death |
| --- | --- | --- | --- | --- |
| Chlordi- | s.c. | 18.38 (16.62–20.32) | 11.31 (9.82–13.04) | 6.50 (5.60–7.54) |
| azepoxide | p.o. | 17.15 (13.89–21.17) | 9.19 (6.72–12.56) | 4.59 (3.77–5.59) |
| Oxazepam | s.c. | 4.60 (4.01–5.27) | 2.14 (1.93–2.39) | 2.00 (1.75–2.29) |
|  | p.o. | 4.59 (3.40–6.21) | 1.74 (1.27–2.38) | 2.00 (1.56–2.56) |
| Diazepam | s.c. | 1.41 (1.20–1.66) | 0.44 (0.37–0.52) | 0.66 (0.57–0.76) |
|  | p.o. | 2.83 (1.97–4.06) | 0.65 (0.39–1.07) | 1.00 (0.77–1.31) |
| Lorazepam | s.c. | 0.22 (0.20–0.24) | 0.06 (0.05–0.07) | 0.09 (0.08–0.10) |
|  | p.o. | 0.68 (0.47–0.98) | 0.23 (0.16–0.33) | 0.25 (0.18–0.33) |

The results for a compound of the invention, 9-[3-[4-(4-chlorophenyl)-4-hydroxy-1-piperidinyl]-propyl]-9H-pyrido[3,4-b]-indole-3-carboxylic acid ethyl ester, are as follows:

| Route | Clonic Convulsions | Tonic Convulsions | Death |
| --- | --- | --- | --- |
| s.c. | inactive | 1.12 (0.77–1.63) | inactive |
| p.o. | inactive | >16.0 | inactive |

For confirmation of this potent anticonvulsant activity, the same compound is examined in the mouse minimal/maximal electroshock test, which is carried out as follows:

MINIMAL/MAXIMAL ELECTROSHOCK

Male CF-1 mice (21–25 gram) are injected intraperitoneally with 1.0, 2.0, 4.0, 8.0, and 16.0 mg base/kg test compound or the 0.25% vehicle Tween 80 ® one half hour prior to the test (8 mice/dose). Shock is applied by placing the animals eyes in contact with an electrode surface that had been previously saturated with saline. Two shock levels are used; a maximum level equivalent to 18 mA, 0.2 sec. and a minimum level equivalent to 8 mA, 0.2 sec. The number of tonic convulsions are used as a measure of anticonvulsant and seizure threshold activity with the determination of the Spearman-Karber estimate of the ED$_{50}$ with 95% confidence intervals.

The results of the maximal/minimal electroshock test for the compound tested, 9-[3-[4-(4-chlorophenyl)-4-hydroxy-1-piperidinyl]-propyl]-9H-pyrido[3,4-b]-indole-3-carboxylic acid ethyl ester show that the compound antagonized maximal electroshock convulsions (ED$_{50}$ and 95% confidence interval: 3.36 (2.05–5.52) mg/kg intraperitoneally) while not affecting minimal electroshock. These results indicate that the compound possesses anticonvulsant activity without the ability to lower the threshold for the induction of convulsions, i.e., it is not a convulsant or a proconvulsant.

EXAMPLE 3

In order to assess possible anxiolytic activity for the compound of Example 1, it is examined in the modified Geller-Seifter Experimentally-Induced Conflict Behavior test, which is carried out as follows:

Male, Sprague-Dawley rats, maintained on a 23 hour food deprivation schedule at approximately 80% body weight, are first given lever-pressing training for a liquid food reward (0.2 cc of 1 part condensed milk to 2 parts of water) obtainable initially for every lever press and later at random intervals, one every two minutes on the average (2-minute Variable Interval [VI]). Experimental sessions are of 69 minutes duration Monday through Thursday. When lever-pressing rates stabilize on the VI-2 minute schedule, three minute tone periods are introduced approximately every 15 minutes. During the tone period, the reinforcement schedule is changed to one in which the milk reward is delivered after every lever press (Continuous Reinforcement [CRF]). After rates stabilize, a grid shock (0.25 sec.) is also delivered after every press during the tone period. The shock intensity is gradually increased until the desired number of responses occur during the tone. Daily sessions continue until the rat has a stable rate during the VI portion and the desired rate during the CRF-tone period. Total responses during the VI and during the tone-period and VI reinforcements are separately recorded by computer. Also, bar presses, reinforcements and tone period responses are recorded on commulative recorders. Drugs are administered prior to a daily session and rates are compared with pre-drug records. Increases in responses during the tone period are taken to indicate anti-anxiety effects, decreases in VI responding indicate side effects (e.g. sedation).

When tested in this procedure, the compound of Example 1 showed no anxiolytic effect over the dose range of 0.5–10.0 mg/kg intraperitoneally and sedation occurred only at doses of 5.0 and 10.0 mg/kg.

EXAMPLE 4

The compound of Example 1 is also tested to determine its in vivo dopamine blocking activity and thereby evaluate its potential as an antipsychotic agent. This test is performed as follows:

Test compounds, suspended or solubilized in 0.25% Tween 80 ® in water, are administered at several dose levels to 20–25 gm male CF-1 mice (6/dose level). Mice are tested one week before the experiment for a positive stereotyped response to 10 mg/kg s.c. apomorphine. A control group, run simultaneously with drug groups, receives equal volumes of solvent. Thirty minutes later (i.p. administration) or 60 minutes later (p.o. administration), drug-treated and control mice are challenged with 10 mg/kg apomorphine s.c. Five minutes after the injection, the rearing-head-bobbing-licking syndrome induced by apomorphine is recorded as present or absent for each animal. Readings are repeated every 5 minutes during a 30 minute test session.

The number of positive or negative 5-minute intervals during which apomorphine-induced stereotyped behavior is present or absent.

ED$_{50}$ values (with 95% confidence intervals) are calculated for inhibition of apomorphine-induced stereotyped behavior by a simple linear regression analysis with inverse prediction.

The ED$_{50}$ and 95% confidence interval, mg/kg, for standard compounds in this procedure are as follows:

| Drug | Intraperitoneal | Oral |
| --- | --- | --- |
| Haloperidol | 1.37 (0.88–2.34) | 2.30 (1.45–3.67) |
| Chlorpromazine | 8.48 (4.79–16.38) | 16.34 (10.14–29.63) |

| Drug | Intraperitoneal | Oral |
|---|---|---|
| Clozapine | 30.06 (19.42–48.21) | 30.72 (19.53–50.33) |

The compound of Example 1 following subcutaneous administration is inactive in this procedure, thereby evidencing a low potential for antipsychotic activity.

EXAMPLE 5

The compound of Example 1 is tested for its ability to inhibit benzodiazepine receptor binding. The β-carbolines generally exhibit a very strong inhibition of receptor binding.

This procedure is performed in the following manner:

Several rats are decapitated and the brains are rapidly removed. Cortical tissue is dissected and homogenized on ice in 50 volumes of buffer (50 mM Tris-HCl, 120 mM NaCl, 5 mM KCl, pH 7.4) by a Polytron homogenizer at half-speed for 1 minute. The homogenate is then centrifuged at 30,000×g for 10 minutes and the supernatant is discarded. The pellet is resuspended in an equal volume of fresh buffer and centrifuged again, and the supernatant is again discarded. The pellet is again resuspended in the same volume of fresh buffer and centrifuged as before, again the supernatant is discarded. The pellet is now resuspended in ⅔ of the previous volume of buffer, and the protein content is assayed by the method of Lowry. The homogenate is stored frozen at −70° C. until use.

One-tenth ml of the homogenate (0.2–0.3 mg protein) is incubated with 3.5 nM ³H-diazepam (New England Nuclear) and various concentrations of test drug in a final volume of 0.5 ml of assay buffer (50 mM Tris-HCl, pH 7.4) for 1 hour on ice. At the end of the incubation, 3 ml of cold buffer are added to each tube, and the contents are rapidly vacuum-filtered through Whatman GF/B glass-fiber filters. The filters are then rapidly washed 3 times with 5 ml of cold buffer, placed in scintillation vials, and shaken for 15 minutes with 10 ml of Hydrofluor (National Diagnostics) scintillation cocktail. The vials are then counted in a Packard 460 CD scintillation counter.

Specific binding is defined as total binding less binding in the presence of 3 μM lorazepam. Binding in the presence of various concentrations of test drug is expressed as a percent of specific binding when no drug is present. These results are then plotted as logit % binding vs log concentration of test drug. Linear regression analysis then yields a straight line with 95% confidence limits from which an IC$_{50}$ can be inversely predicted. K$_i$ (inhibition constant) for the test drug is then calculated by the formula:

$$K_i = \frac{IC_{50}}{1 + \frac{[^3H-\text{Diazepam}]}{K_D}}$$

where K$_D$ for ³H-diazepam binding = 3.5 nM.

The activity of standard benzodiazepines in this test (and their 95% confidence interval) are as follows:

Lorazepam: K$_i$ = 2.4 (2.0–2.7) nM
Diazepam: K$_i$ = 3.7 (2.8–5.3) nM

When tested in this procedure, the compound of Example 1 gives an inhibition constant (K$_i$) of 2.3 (1.2–6.0) μM or 2300 nM, showing the compound to be very weak in the inhibition of benzodiazepine receptor binding. This is a surprising result in light of the generally potent inhibitory effect the β-carbolines exhibit in this procedure.

The total neuropharmacological profile presented by the procedures and results of Examples 2–5 show that compounds of the invention, such as that of Example 1, are unique in exhibiting potent anticonvulsant activity while being devoid of anxiolytic and antipsychotic properties, having negligible sedative activity and showing very weak inhibition of benzodiazepine receptor binding. Such compounds are of significant value in the treatment of various seizure conditions.

What is claimed is:

1. A compound having the formula

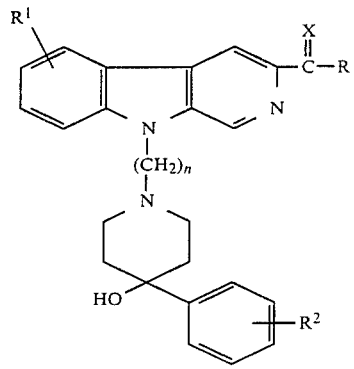

wherein

X is O, S or NHR³, wherein R³ is hydrogen, lower alkyl or cycloalkyl;

R is loweralkyl, loweralkoxy, aralkoxy of up to 10 carbon atoms or NR⁴R⁵ wherein R⁴ and R⁵ are, independently, hydrogen, lower alkyl, cycloalkyl or aminoalkyl; or R is alkoxymethyl or hydroxymethyl;

n is one of the integers 2, 3 or 4;

R¹ and R² are, independently, hydrogen, halo, nitro, cyano, SCH₃, or NR⁶R⁷, NHCOR⁶, COOR⁶, OR⁶ or SO₂NR⁶R⁷ wherein R⁶ and R⁷ are independently hydrogen or loweralkyl.

2. The compound of claim 1 which is 9-[3-[4-(4-chlorophenyl)-4-hydroxy-1-piperidinyl]-propyl]-9H-pyrido[3,4-b]indole-3-carboxylic acid ethyl ester.

* * * * *